United States Patent
Ueyama et al.

(10) Patent No.: US 10,444,162 B2
(45) Date of Patent: Oct. 15, 2019

(54) METHOD OF TESTING AN OBJECT AND APPARATUS FOR PERFORMING THE SAME (71) Applicant: SAMSUNG ELECTRONICS CO., LTD., Suwon-si, Gyeonggi-Do (KR)

(72) Inventors: Shinji Ueyama, Kawasaki (JP); Masato Kajinami, Tokyo (JP); Tatsuya Ishimoto, Yokohama (JP)

(73) Assignee: SAMSUNG ELECTRONICS CO., LTD., Suwon-si, Gyeonggi-Do (KR)

(*) Notice: Subject to any disclaimer, the term of this patent is extended or adjusted under 35 U.S.C. 154(b) by 0 days.

(21) Appl. No.: 15/938,570

(22) Filed: Mar. 28, 2018

(65) Prior Publication Data

US 2018/0284032 A1 Oct. 4, 2018

(30) Foreign Application Priority Data

Apr. 3, 2017 (JP) ................................ 2017-073703
Oct. 25, 2017 (KR) ........................ 10-2017-0139624

(51) Int. Cl.
G01N 21/88 (2006.01)
H01L 21/67 (2006.01)
(Continued)

(52) U.S. Cl.
CPC ..... *G01N 21/8806* (2013.01); *G01B 11/0608* (2013.01); *G01B 11/25* (2013.01);
(Continued)

(58) Field of Classification Search
CPC ............ H01L 22/12; H01L 21/67288; H01L 21/68764; H01L 21/67242; H01L 22/24;
(Continued)

(56) References Cited

U.S. PATENT DOCUMENTS 7,038,767 B2 5/2006 Toyoshima et al.
7,196,782 B2 3/2007 Fielden et al.
(Continued)

FOREIGN PATENT DOCUMENTS

KR 10-0851212 8/2008
KR 1020150021049 2/2015
KR 1020160045137 4/2016

*Primary Examiner* — Tri T Ton
(74) *Attorney, Agent, or Firm* — F. Chau & Associates, LLC (57) ABSTRACT An apparatus for testing an object includes a moving unit configured to hold and move the object. A transmissive illuminating unit includes a light source generating light and a transmissive mask pattern. The transmissive mask pattern includes a first region configured to convert the light generated from the light source into a slit light, and a second region arranged in a movement direction of the object with respect to the first region to partially transmit the light generated from the light source. The transmissive illuminating unit is configured to project a measuring light, which is provided by transmitting the light generated from the light source through the transmissive mask pattern, to the object. A detecting unit is configured to receive a reflected light of the measuring light from the object and to detect a height and surface state of the object based on the reflected light.

14 Claims, 13 Drawing Sheets (51) Int. Cl.
*H01L 21/66* (2006.01)
*G01B 11/30* (2006.01)
*G01N 21/94* (2006.01)
*G01N 21/95* (2006.01)
*G01B 11/06* (2006.01)
*G01B 11/25* (2006.01)
*H01L 21/687* (2006.01)

(52) U.S. Cl.
CPC ............ *G01B 11/303* (2013.01); *G01N 21/94* (2013.01); *G01N 21/9505* (2013.01); *H01L 21/67288* (2013.01); *H01L 22/12* (2013.01); *G01N 2021/8848* (2013.01); *G01N 2021/945* (2013.01); *H01L 21/68764* (2013.01)

(58) Field of Classification Search
CPC ... G01B 11/303; G01B 11/0608; G01B 11/25; G01N 2021/8848; G01N 2021/945; G01N 21/8806; G01N 21/94; G01N 21/9505; G03F 7/70141

USPC .................................................. 356/600–640
See application file for complete search history.

(56) References Cited

U.S. PATENT DOCUMENTS

| | | | |
|---|---|---|---|
| 8,189,195 B2* | 5/2012 | Den Boef | G03F 7/7065 356/237.5 |
| 9,097,645 B2 | 8/2015 | Cai et al. | |
| 9,513,228 B2 | 12/2016 | Shibata et al. | |
| 9,709,390 B2 | 7/2017 | Luxen et al. | |
| 2005/0173752 A1* | 8/2005 | Chung | H01L 21/2026 257/315 |
| 2009/0161082 A1* | 6/2009 | Sakamoto | G03F 7/70341 355/18 |

* cited by examiner

METHOD OF TESTING AN OBJECT AND APPARATUS FOR PERFORMING THE SAME

CROSS-RELATED APPLICATION

This application claims priority under 35 USC § 119 to Japanese Patent Application No. 2017-073703, filed on Apr. 3, 2017 in the Japanese Intellectual Property Office and to Korean Patent Application No. 10-2017-0139624 filed on Oct. 25, 2017 in the KIPO, the contents of which are herein incorporated by reference in their entirety.

TECHNICAL FIELD

The present disclosure relates to testing and, more specifically, to a method of testing an object and an apparatus for performing the same.

DISCUSSION OF THE RELATED ART

In testing a semiconductor chip, during manufacturing, it is often desirable to detect a mount height of the semiconductor chip. To perform this test, an object may be exposed to light through a slit. The light is then reflected off of the object and this reflected light is detected using a sensor. The sensor data may then be analyzed to detect the mount height of the semiconductor chip. If the detected mount height is not a predetermined design range, the mount height may be adjusted, or the semiconductor chip may be rejected.

Further, semiconductor chips may be tested to detect particles that may be present on a surface thereof or to detect other problems with the surface of the semiconductor chip, as particles may come to rest on the semiconductor chips after mounting and/or other complications may emerge as a result of mounting. This testing may also be performed using light, for example, visible light.

In general, separate testing units are used for performing each of the above-mentioned tests. For example, a first testing unit may be used to test mount height while a second, different, testing unit may be used to detect the presence of surface particles. This use of separate testing units may add cost, complexity, and time to the fabricating and testing of semiconductor chips.

SUMMARY

An apparatus for testing an object includes a moving unit configured to hold and move the object. A transmissive illuminating unit includes a light source generating light and a transmissive mask pattern. The transmissive mask pattern includes a first region configured to convert the light generated from the light source into a slit light, and a second region arranged in a movement direction of the object with respect to the first region to partially transmit the light generated from the light source. The transmissive illuminating unit is configured to project a measuring light, which is provided by transmitting the light generated from the light source through the transmissive mask pattern, to the object. A detecting unit is configured to receive a reflected light of the measuring light from the object and to detect a height and surface state of the object based on the reflected light.

A method of testing an object uses a moving unit, a transmissive illuminating unit, and a detecting unit. The moving unit is configured to hold and move the object. The transmissive illuminating unit includes a light source generating light and a transmissive mask pattern. The transmissive mask pattern has a first region configured to convert the light generated from the light source into a slit light, and a second region arranged in a movement direction of the object with respect to the first region to partially transmit the light generated from the light source. The transmissive illuminating unit is configured to project a measuring light, which is provided by transmitting the light generated from the light source through the transmissive mask pattern, to the object. The method includes acquiring a reflected light of the measuring light from the object using the detecting unit and detecting a height and surface state of the object based on the reflected light acquired by the detecting unit.

An apparatus for testing semiconductor chips includes a stage configured to hold the semiconductor chips and to move in a movement direction. A light source is configured to generate light of a first brightness, to generate light of a second brightness different from the first brightness, and to cast the light of the first and second brightness onto the semiconductor chips as they are moved by the stage. A first light detecting unit is configured to receive the light of the first brightness that is reflected off of the semiconductor chips and to determine a mounted height therefrom. A second light detecting unit is configured to receive the light of the second brightness that is reflected off of the semiconductor chips and to detect particles present on the semiconductor chips therefrom.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings, wherein.

DETAILED DESCRIPTION OF THE EMBODIMENTS

In describing exemplary embodiments of the present disclosure illustrated in the drawings, specific terminology is employed for sake of clarity. However, the present disclosure is not intended to be limited to the specific terminology so selected, and it is to be understood that each specific element includes all technical equivalents which operate in a similar manner.

Figure 1:
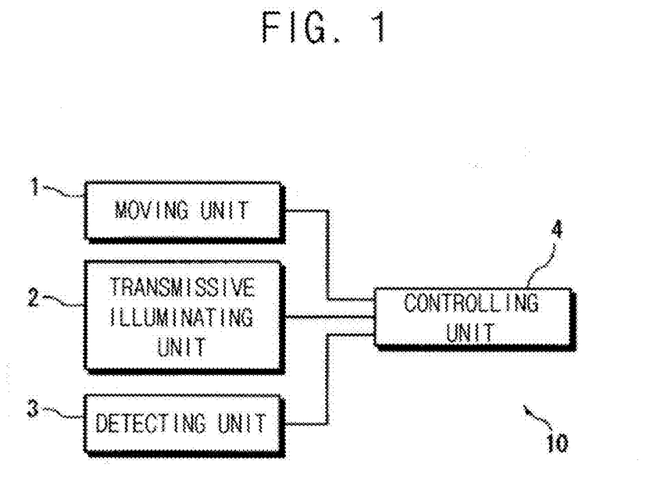
FIG. 1 is a block diagram illustrating an apparatus for testing an object in accordance with exemplary embodiments of the present disclosure.
Figure 2:
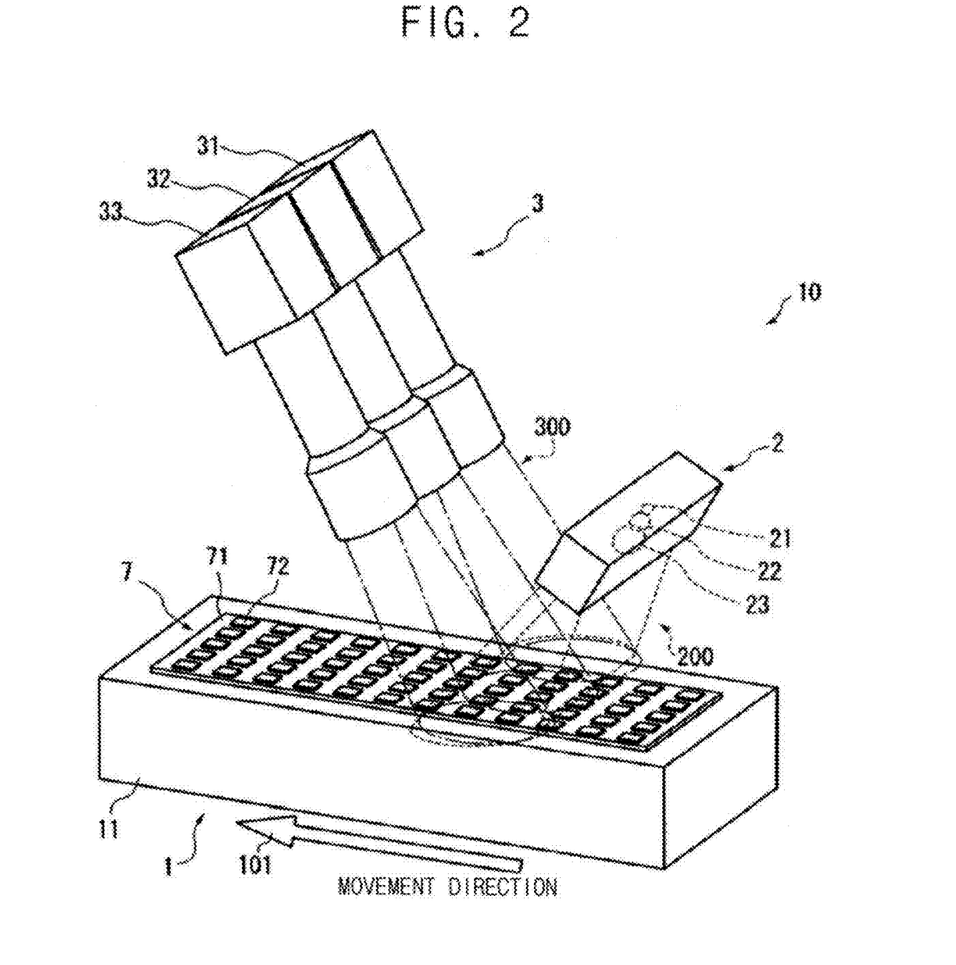
FIG. 2 is a perspective view illustrating the apparatus in FIG. 1.
Figure 3:
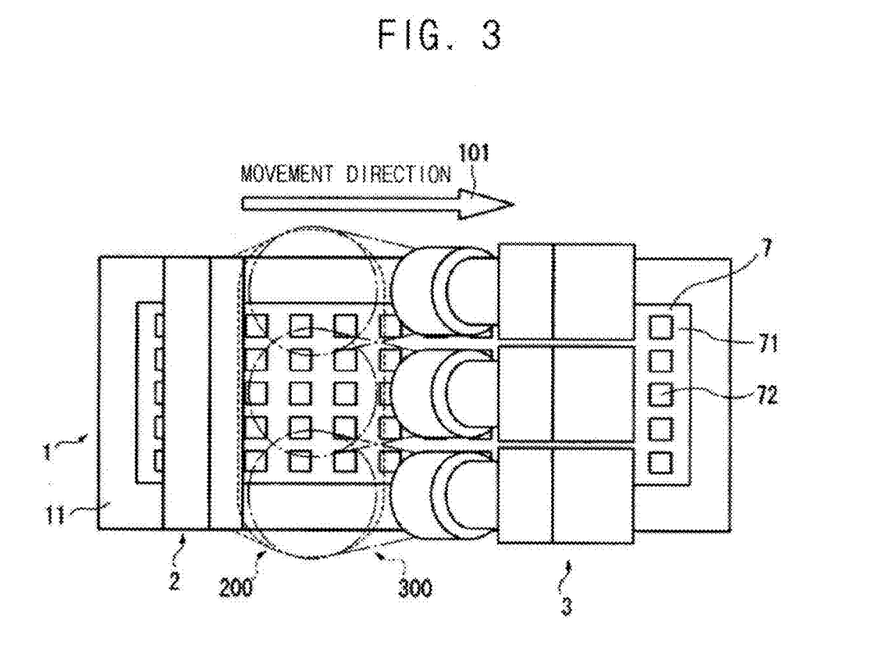
FIG. 3 is a plan view illustrating the apparatus in FIG. 2.
Figure 4:
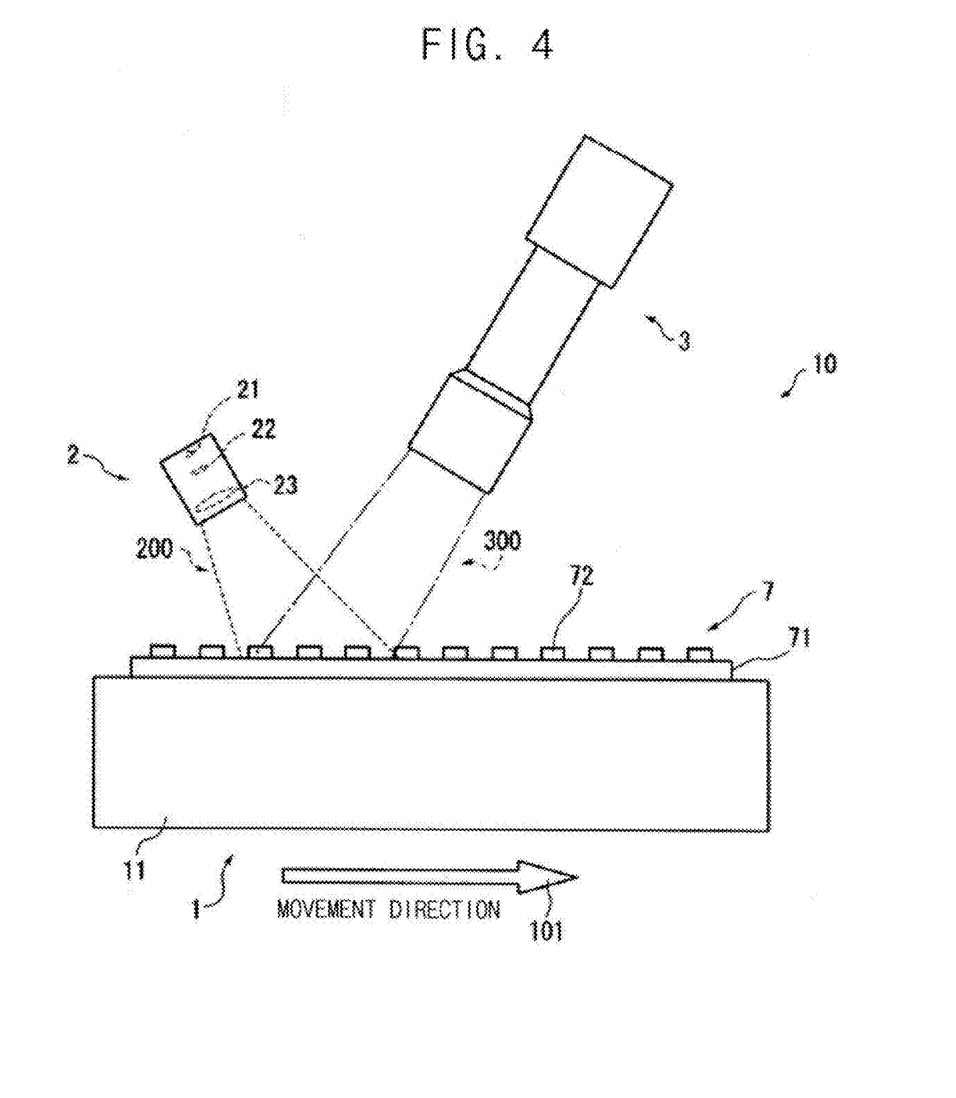
FIG. 4 is a front view illustrating the apparatus in FIG. 2.
Figure 5:
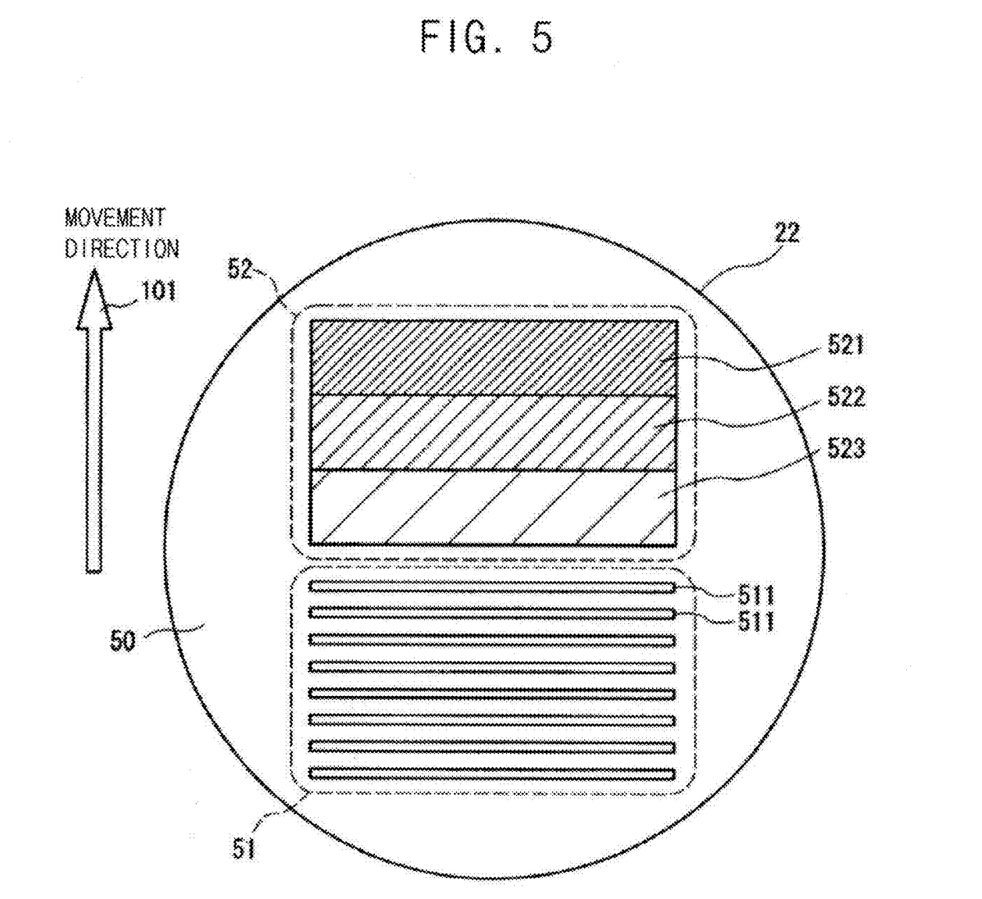
FIG. 5 is a plan view illustrating a transmissive mask pattern in FIG. 2 in accordance with exemplary embodiments of the present disclosure.
Figure 9:
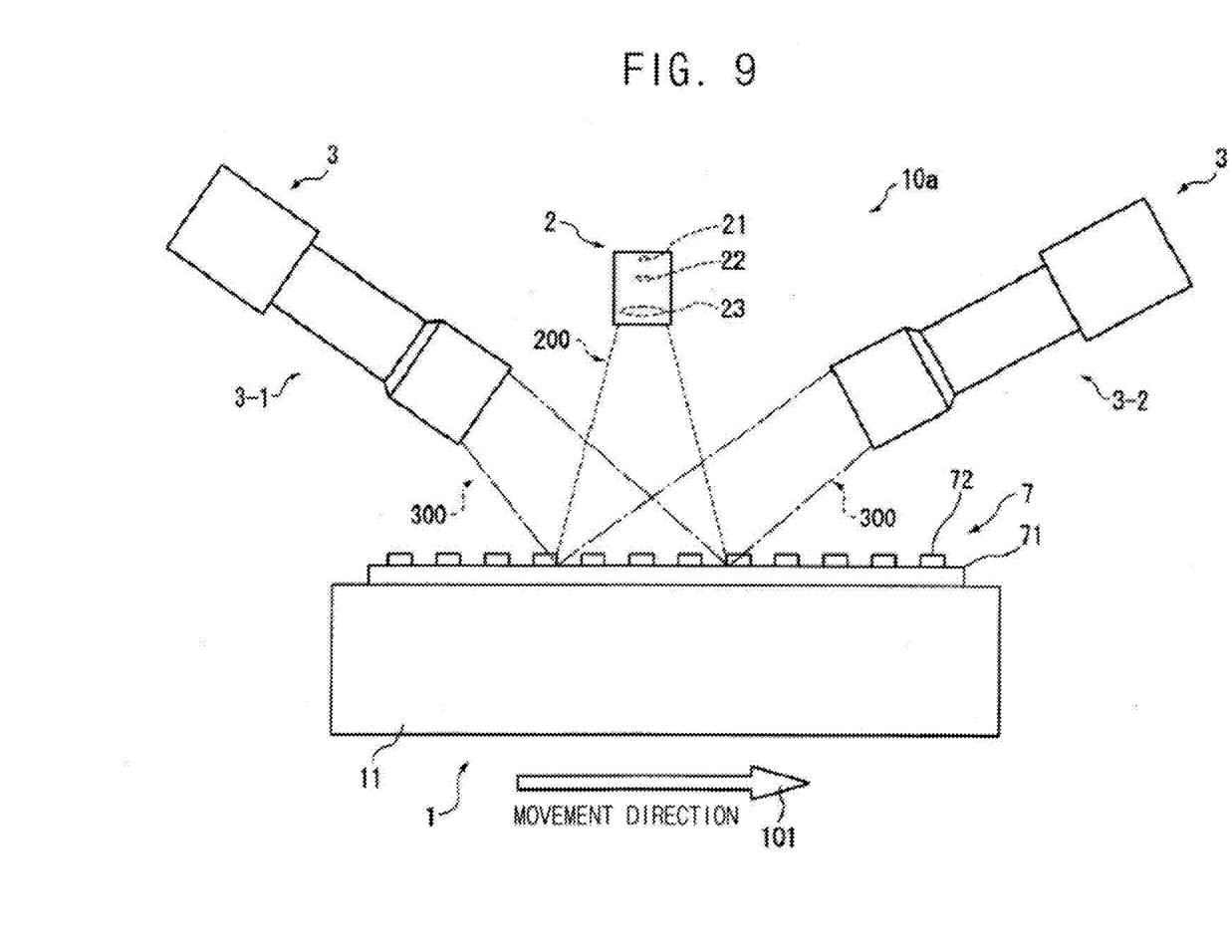
FIG. 9 is a front view illustrating the apparatus in FIG. 2 in accordance with exemplary embodiments of the present disclosure.

FIG. 1 is a block diagram illustrating an apparatus for testing an object in accordance with exemplary embodiments of the present disclosure. FIG. 2 is a perspective view illustrating the apparatus in FIG. 1. FIG. 3 is a plan view illustrating the apparatus in FIG. 2. FIG. 4 is a front view illustrating the apparatus in FIG. 2. FIG. 5 is a plan view illustrating a transmissive mask pattern in FIG. 2 in accordance with exemplary embodiments of the present disclosure, and FIG. 9 is a front view illustrating the apparatus in FIG. 2 in accordance with exemplary embodiments of the present disclosure.

Referring to FIG. 1, an apparatus 10 for testing an object in accordance with exemplary embodiments of the present disclosure may include a moving unit 1, a transmissive illuminating unit 2, a detecting unit 3, and a controlling unit 4.

The controlling unit 4 may be configured to control the moving unit 1, the transmissive illuminating unit 2, and the detecting unit 3. The controlling unit 4 may be configured to mediate, and otherwise communicate, information between the moving unit 1, the transmissive illuminating unit 2, and the detecting unit 3. The controlling unit 4 may be configured to determine whether an object 7 (FIG. 2) may be properly mounted based on information obtained by the detecting unit 3.

Referring to FIG. 2, the moving unit 1 may be configured to secure the object 7 to a stage 11. The moving unit 1 may be configured to move the stage 11 at a constant speed in a movement direction indicated by an arrow 101, thereby moving the object 7. The object 7 may include a printed circuit board (PCB) 71. A plurality of semiconductor chips 72 may be mounted on the PCB 71. However, the object 7 might not include the PCB 71, and instead may include a different object under test. The moving unit 1 may transmit coordinate information representing movement positions of the stage 11 to the detecting unit 3 through the controlling unit 4. The detecting unit 3 may synchronize the coordinate information representing the movement positions of the stage 11 to obtain an image-capturing timing.

Referring to FIGS. 2 and 4, the transmissive illuminating unit 2 may include a light source 21, a transmissive mask pattern 22, and a lens 23. The light source 21 may include a visible-light laser, an LED, etc. The lens 23 may include a telecentric lens.

Referring to FIG. 5, the transmissive mask pattern 22 may include a shading region 50, a first region 51, and a second region 52. The first region 51 and the second region 52 may be arranged in the movement direction 101 of the object 7. The shading region 50 may be configured to at least partially shade light emitted from the light source 21. The first region 51 may have a plurality of slits 511. Light emitted from the light source 21 may pass through the slits 511 and be converted into a plurality of slit lights. The slit lights generated by the first region 51 may be used for detecting a height of the semiconductor chips 72 using a light cut method. The second region 52 may partially transmit the light emitted from the light source 21 to provide a proper brightness of light for photographing an image, for example, a two-dimensional image. The slit light used for the light cut method may be relatively bright. In contrast, a light for photographing an image may be less bright than the slit light. Thus, the brightness of light transmitting through the second region 52 may be restricted by controlling a light transmissivity (first factor of transmission characteristics) through the second region 52. Referring back to FIG. 2, the transmissive illuminating unit 2 may project a measuring light 200, which may be generated by passing the light emitted from the light 21 through the transmissive mask pattern 22 and the lens 23, to the object 7.

Referring again to FIG. 5, the second region 52 of the transmissive mask pattern 22 may include a plurality of sub-regions 521, 522, and 523 each having different light transmission characteristics. The sub-regions 521, 522, and 523 may be arranged in the movement direction 101 of the object 7. The sub-regions 521, 522, and 523 may each have different shades, either in terms of gray scale or half-tone. The sub-regions 521, 522, and 523 may have different light transmissivities. The light transmissivity within the sub-region 521 may be uniform. The light transmissivity within the sub-region 522 may be uniform. The light transmissivity within the sub-region 523 may be uniform. The brightness of light projected to the object 7 may be changed by a uniform range, for example, by differentiating the light transmissivities of the sub-regions 521, 522, and 523 from each other. Thus, the brightness of a reflected light 300 that may reflect off of the object 7 may be changed by moving the object 7 (see, for example, FIG. 2). Although different brightnesses of light may be needed to detect particles, cracks, etc., on the object 7, exemplary embodiments of the present invention may be able to perform each test with a single apparatus 10 by establishing a brightness of light that is suitable for detecting the particles, the cracks, etc., on the object 7.

According to exemplary embodiments of the present disclosure, the second region 52 may be a single continuous region. Alternatively, the second region 52 may include two sub-regions or four sub-regions. The first region 51 may have one slit 511 arranged in a lengthwise direction substantially perpendicular to the movement direction 101. Alternatively, the first region 51 may have multiple slits 511 arranged in lengthwise and breadthwise directions.

The detecting unit 3 may include at least one camera and an image processor for processing an image acquired by the camera. The detecting unit 3 may receive the reflected light 300 that is formed by reflecting the measuring light 200 on the object 7. The detecting unit 3 may detect a height and surface state of the object 7 based on the reflected light 300. As may be seen in FIGS. 2 to 4, the detecting unit 3 may include three cameras 31, 32, and 33 that may be arranged in a vertical direction. The cameras 31, 32, and 33 may each include a complementary metal oxide semiconductor (CMOS) sensor, and/or a charged coupled device (CCD) sensor having an optical device in which a telecentric lens may be installed.

The configurations of the apparatus 10 in FIG. 1 may have an alternative configuration from that illustrated in FIGS. 2 to 4. For example, an apparatus 10a may have the configuration illustrated in FIG. 9. Referring to FIG. 9, the measuring light 200 from the transmissive illuminating unit 2 may be directed to the object 7 from a position over the object 7. Cameras 3-1 and 3-2 of the detecting unit 3 may be arranged at a front position and a rear position in the movement direction 101, respectively. The cameras 3-4 and 3-2 may each have configurations substantially the same as those of the cameras 31, 32, and 33 in FIG. 2. The apparatus 10a may accordingly be configured to reduce a non-measured region (referred to as an occlusion). In FIG. 9, the same reference numerals may refer to corresponding elements in FIGS. 2 to 4.

The cameras 31, 32, and 33 may each be configured to photograph the reflected light 300 of the measuring light 200 transmitting the second region 52 in FIG. 2 to generate three images (two-dimensional images) having different brightnesses. The detecting unit 3 may perform an image identification process based on the three images having the different brightnesses to detect the surface state of the object 7. The cameras 31, 32, and 33 may each be configured to photograph the reflected light 300 of the measuring light 200 transmitting the first region 51 in FIG. 5 to generate an image 700 in FIG. 8.

Figure 8:
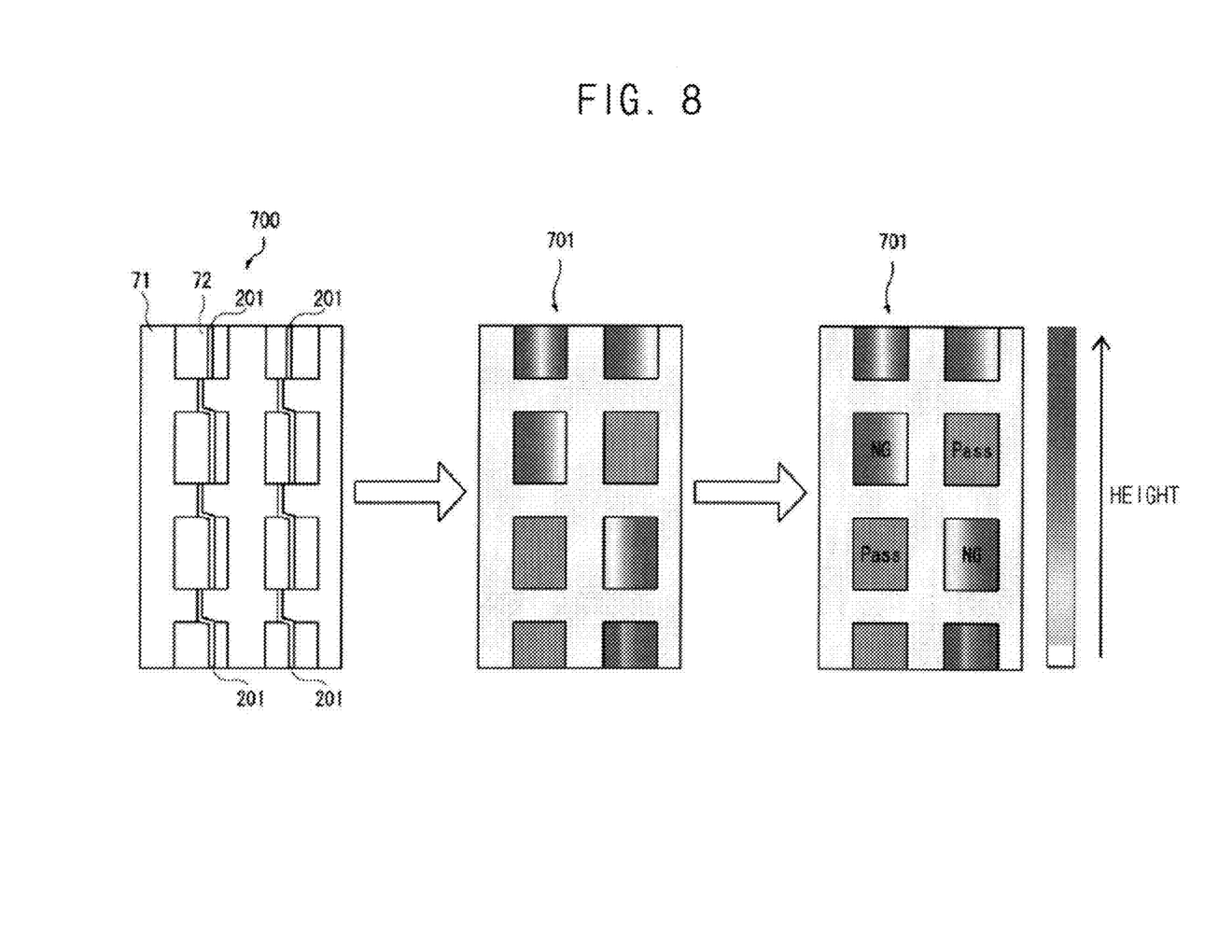
FIG. 8 is a front view illustrating operations of the apparatus in FIG. 1.

FIG. 8 illustrates examples of the detecting unit 3. For example, FIG. 8 illustrates the image 700 photographed by the cameras 31, 32, and 33, a three-dimensional image 701 of the object generated by the detecting unit 3 based on the image 700, and determination results with respect to the three-dimensional image 701. The image 700 may include a transmitted shape of the slit light 201 on the PCB 71 and the semiconductor chip 72. The slit light 201 may be generated by passing the light through the slit 511 in the first region 51 in FIG. 5. The detecting unit 3 may generate the three-dimensional image 701 by the light cut method based on the images 700 and the coordinate information of the stage 11. The three-dimensional image 701 may be obtained by gradating a color having the height information on the image 700. The detecting unit 3 or the controlling unit 4 may compare the mount state of the semiconductor chip 72 with a reference state based on the three-dimensional image 701 to determine whether the mounting of the semiconductor chip 72 is normal. For example, when a slant angle may be narrow, or the height may be within an allowable range, the mounting of the semiconductor chip 72 may be determined to be normal. In contrast, when the slant angle may be wide, or the height may not be within the allowable range, the mount of the semiconductor chip 72 may be determined to be abnormal. Pixels of the cameras 31, 32, and 33 and the coordinate information of the stage 11 may be corrected. Thus, the detecting unit 3 may align the image based on the reflected light 300 of the measuring light 200 passing through the first region 51 with the image based on the reflected light 300 of the measuring light 200 passing through the second region 52. Therefore, the detecting unit 3 may link the height information of the object 7 with the detection results of the surface state on the object 7 to determine the mounting state of the object 7.

Figure 10:
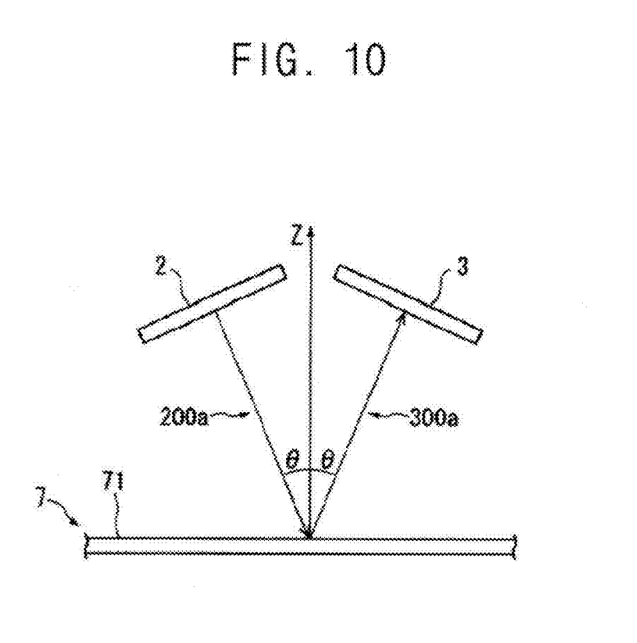
FIG. 10 is a front view illustrating the apparatus in FIG. 2 in accordance with exemplary embodiments of the present disclosure.
Figure 11:
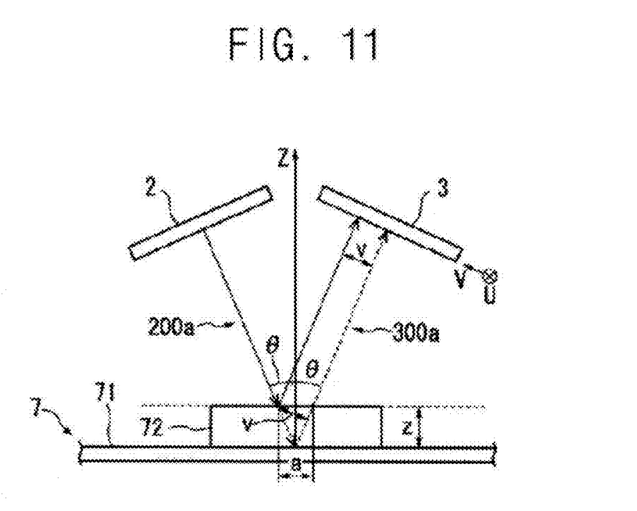
FIG. 11 is a front view illustrating the apparatus in FIG. 2 in accordance with exemplary embodiments of the present disclosure.
Figure 12:
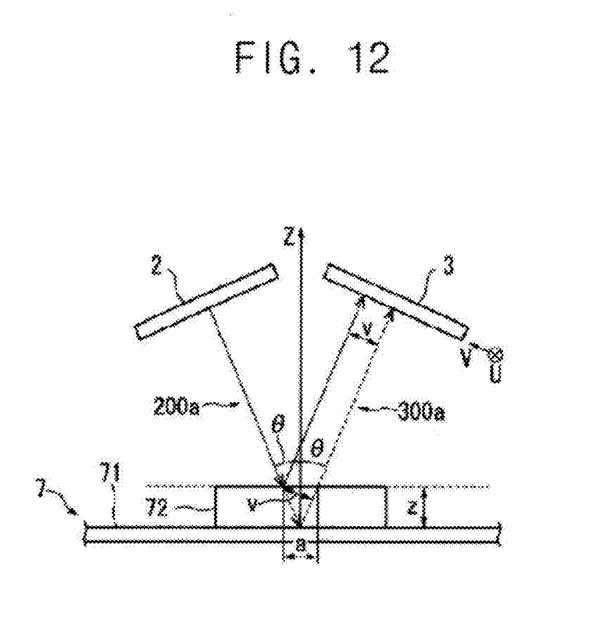
FIG. 12 is a front view illustrating operations of the apparatus in FIG. 1.

Hereinafter, a method of measuring a height of the object 7 using the light cut method may be illustrated with reference to FIGS. 10 to 14. The same reference numerals in FIGS. 10 to 12 may refer to corresponding elements in FIGS. 2 to 4. FIGS. 10 to 12 may illustrate positional relationships between the transmissive illuminating unit 2, the detecting unit 3, and the PCB 71 as the object 7. The positional relationships in FIGS. 10 to 12 may be substantially same.

Referring to FIGS. 10 to 12, the slit light 200a emitted from the light source 21 of the transmissive illuminating unit 2 may be projected to the object 7. The slit light 200a may be regularly reflected from the object 7. The detecting unit 3 may detect a reflected light 300a reflected from the object 7.

According to exemplary embodiments of the present disclosure, a projected angle θ of the slit light 200a, which may be projected from the transmissive illuminating unit 2, with respect to the PCB 71, may be substantially the same as a reflected angle θ of the reflected light 300a with respect to the PCB 71. For example, an angle θ between the light source 21 and a vertical axis Z may be substantially the same as an angle θ between the detecting unit 3 and the vertical axis Z. However, the angle θ between the light source 21 and a vertical axis Z may be different from the angle θ between the detecting unit 3 and the vertical axis Z.

FIG. 10 illustrates the slit light 200a projected to the surface of the PCB 71 and the reflected light 300a, which may be reflected from the PCB 71, photographed by the detecting unit 3. FIG. 11 illustrates the slit light 200a projected to the surface of the semiconductor chip 72 on the PCB 71 and the reflected light 300b, which may be reflected from the semiconductor chip 72, photographed by the detecting unit 3. FIG. 12 illustrates configurations substantially the same as those in FIG. 11.

Referring to FIG. 11, when a height z of the object 7 may be changed, a detection spot of the detecting unit 3 may be changed by a distance v. A relationship between the distance v and the height z may be represented by Formula 1. A height of the PCB 71 may be zero.

$$v = 2z \sin \theta \qquad \text{Formula 1}$$

Referring to FIG. 12, a distance a between a position of the slit light 200a reflected from the semiconductor chip 72 having the height z and a position of the reflected light 300a at the height z from the PCB 71 may be represented by Formula 2.

$$a = 2z \tan \theta \qquad \text{Formula 2}$$

The distance v may be obtained from Formula 1 and Formula 3.

$$v = a \cos \theta = 2z \tan \theta \cos \theta = 2z \sin \theta \qquad \text{Formula 3}$$

Figure 13:
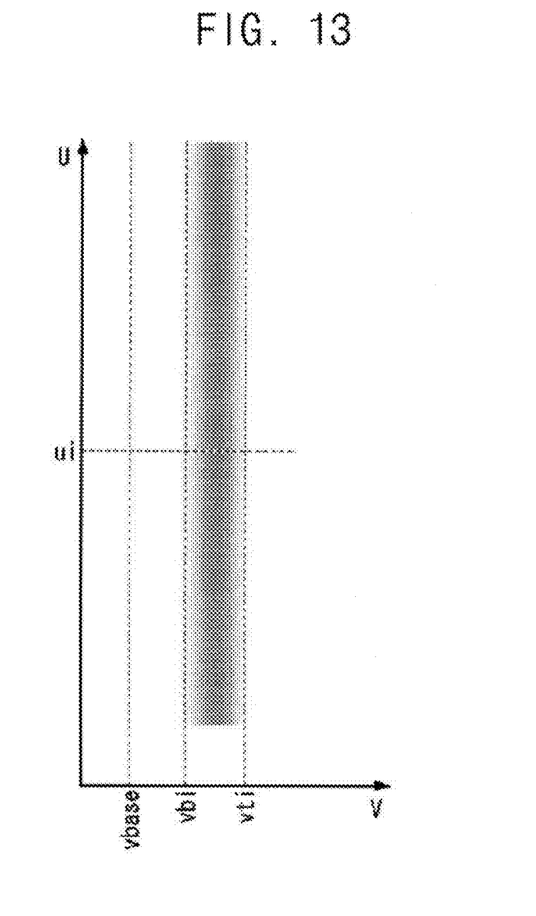
FIG. 13 is a front view illustrating operations of the apparatus in FIG. 1.
Figure 14:
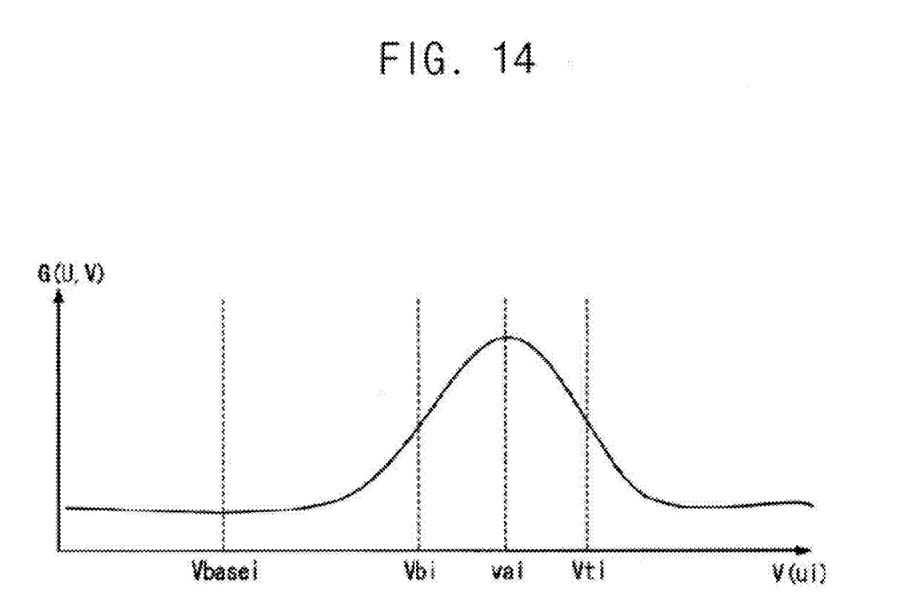
FIG. 14 is a front view illustrating operations of the apparatus in FIG. 1.

Referring to FIGS. 13 and 14, the reflected light 300b photographed by the detecting unit 3 may have uniform luminance distribution. For example, the reflected light 300b may include a band-shaped light having a uniform width. FIG. 13 illustrates an image of the reflected light 300b from the semiconductor chip 72 on a U-V coordinate as a photograph face of the detecting unit 3. The U-axis and the V-axis of the U-V coordinate may be substantially the same as the arrows U and V in FIGS. 11 and 12. The V-axis may be substantially perpendicular to the slit direction, e.g., the lengthwise direction of the slit light 200a. The U-axis may be substantially parallel to the slit direction, e.g., the lengthwise direction of the slit light 200a. In FIG. 13, a horizontal axis may correspond to coordinate values of the V-axis and a vertical axis may correspond to coordinate values of the U-axis. FIG. 13 illustrates luminance of the pixels as brightnesses of the gray scales. Further, the coordinate values abase may correspond to the luminance distribution of the reflected light 300a from the PCB 71. The coordinate values vbi and vti may correspond to an increasing edge and a decreasing edge of the luminance distribution of the reflected light 300b in the coordinate values ui of the U-axis in FIG. 14.

A photographed position of the reflected light 300b may be obtained by an average of center values or half-widths of a profile in the V-axis substantially perpendicular to the slit direction. FIG. 14 illustrates the luminance distribution of the image of the reflected light 300b in the coordinate value ui of the U-axis. A horizontal axis may correspond to the coordinate values of the V-axis in which the U-axis may be constant at the coordinate value ui. A vertical axis may correspond to luminance values G, e.g., a luminance value of each of the pixel in the U-V coordinate. As shown in FIG. 14 an average coordinate value vai of the half-width at the coordinate value ui may be obtained by following Formula 4 using a coordinate value vbi of the increasing edge and a coordinate value vti of the increasing edge.

$$vai=(vbi+vti)/2 \qquad \text{Formula 4}$$

Therefore, a three-dimensional height zi may be obtained by following Formula 5 based on Formula 3 and Formula 4.

$$zi=(vai-v\text{base})/2 \sin \theta \qquad \text{Formula 5}$$

The three-dimensional height zi may include an error caused by lens distortion or brightness variation of the slit light. Thus, the three-dimensional height zi may be corrected using the average coordinate value vai of the half-width by casting the slit light on the object.

According to exemplary embodiments of the present disclosure, the apparatus 10 may simultaneously measure the height of the semiconductor chip using the light cut method and acquire an image of the surface of the semiconductor chip. For example, the image of the surface may be used to obtain the surface state of the object 7, and accordingly, the height and the surface state of the object 7 may be simultaneously obtained. Thus, a distance to the sensor may be reduced to reduce a measurement time. Further, the half-tone or the gray tone may be arranged so that the test may be performed once without adjusting of the brightness with respect to the object having different reflectivities.

Further, the object 7 moved by the moving unit 1 might not be constant. When the object 7 may not be moved at a constant speed, the three-dimensional image 701 may be obtained by the light cut method based on the coordinate information of the moving unit 1 illustrated with reference to FIG. 8.

Hereinafter, a transmissive mask pattern in FIG. 6 may be illustrated. The same reference numerals in FIGS. 5 and 6 may refer to corresponding elements and omitted description may be assumed to be at least similar to that described above for corresponding arrangements.

Figure 6:
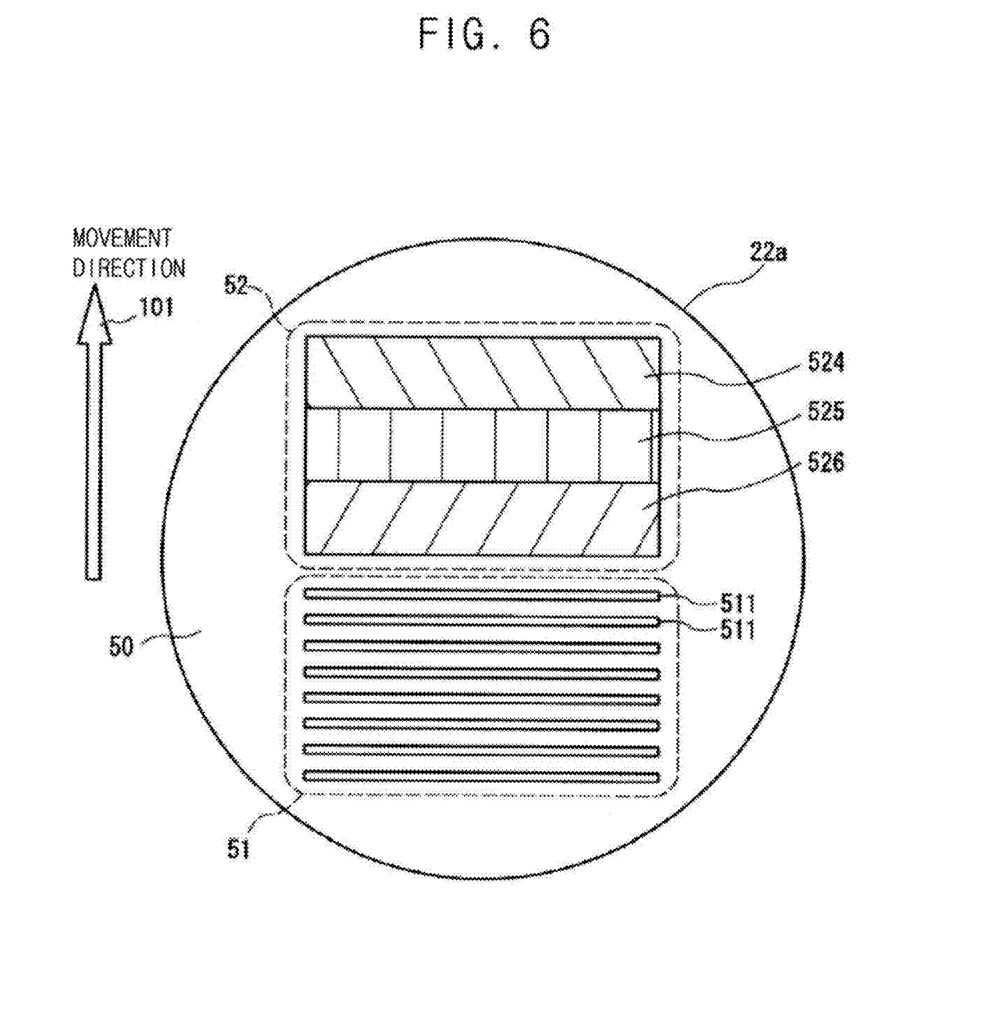
FIG. 6 is a plan view illustrating a transmissive mask pattern in FIG. 2 in accordance with exemplary embodiments of the present disclosure.

Referring to FIG. 6, the transmissive mask pattern 22a may include the second region 52 arranged in the movement direction 101. The second region 52 may include a sub-region 524 having a red filter, a sub-region 525 having a green filter, and a sub-region 526 having a blue filter. The red filter, the green filter and the blue filter may each include a primary color filter corresponding to its color. When the light source 21 may be a white light source, the detecting unit 3 may synthesize the reflected lights 300 of the measuring light 200 transmitting through the color filter by the sub-regions 524, 525, and 526 to generate a color image. Each of the sub-regions 524, 525, and 526 may have a transmissivity for partially restricting the brightness of the light emitted from the light source 21 to provide the light with the proper brightness for photographing the object.

Hereinafter, a transmissive mask pattern in FIG. 7 may be illustrated. The same reference numerals in FIGS. 5 and 7 may refer to corresponding elements and omitted description may be assumed to be at least similar to that described above for corresponding arrangements.

Figure 7:
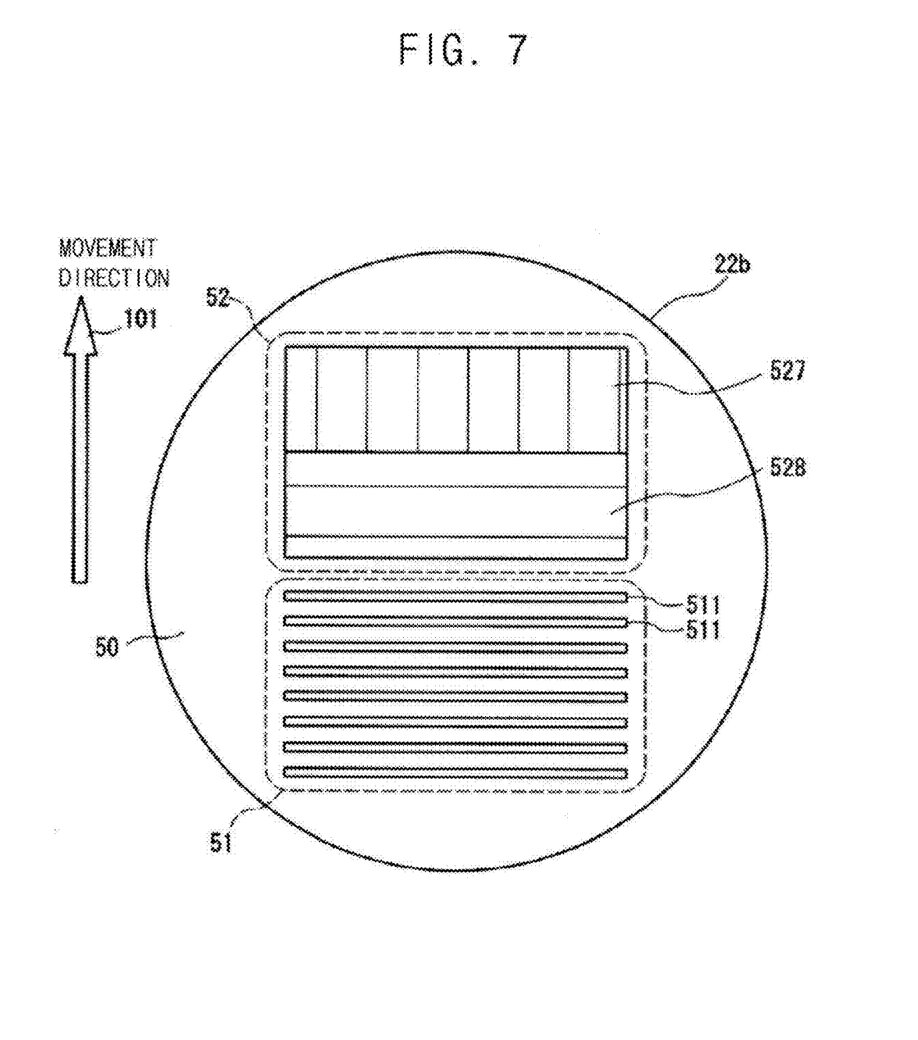
FIG. 7 is a plan view illustrating a transmissive mask pattern in FIG. 2 in accordance with exemplary embodiments of the present disclosure.

Referring to FIG. 7, the transmissive mask pattern 22b may include the second region 52 arranged in the movement direction 101. The second region 52 may include a plurality of sub-regions 527 and a sub-region 528 configured to form polarizers having different polarizing directions. The sub-regions 527 and the sub-region 518 may be configured to transmit light polarized in the vertical or the horizontal direction. The detecting unit 3 may photograph the reflected light 300 of the measuring light 200 transmitting through the sub-regions 527 and 528 to restrict the measuring light 200 to straight polarized light, thereby photographing the surface state of the object 7. Each of the sub-regions 527 and 528 may have a transmissivity for partially restricting the brightness of light emitted from the light source 21 to provide light with the proper brightness for photographing the object.

According to exemplary embodiments of the present disclosure, the moving unit 1 may hold the object 7. The moving unit 1 may move the object at the constant speed. The transmissive illuminating unit 2 may include a light source 21 and a transmissive mask pattern 22. The transmissive mask pattern 22 may have a first region 51 configured to convert the light emitted from the light source 21 into the slit light, and a second region 52 arranged in the movement direction of the object 7 with respect to the first region 51 to partially transmit the light emitted from the light source 21. The illuminating unit 2 may be configured to project the measuring light, which may be generated by transmitting the light from the light source through the transmissive mask pattern 22, to the object 7. Thus, the height and the surface state of the object may be simultaneously obtained using one transmissive illuminating unit 2.

Exemplary embodiments described herein are illustrative, and many variations can be introduced without departing from the spirit of the disclosure or from the scope of the appended claims. For example, elements and/or features of different exemplary embodiments may be combined with each other and/or substituted for each other within the scope of this disclosure and appended claims.

What is claimed is:

1. An apparatus for testing an object, the apparatus comprising:
    a moving stage configured to hold and move the object;
    a transmissive illuminating optical system including a light source generating light and a transmissive mask pattern, the transmissive mask pattern including a first region configured to convert the light generated from the light source into a slit light, and a second region arranged in a movement direction of the object with respect to the first region to partially transmit the light generated from the light source, wherein the transmissive illuminating optical system is configured to project a measuring light, which is provided by transmitting the light generated from the light source through the transmissive mask pattern, to the object; and
    a detector configured to receive a reflected light of the measuring light from the object and to detect a height and surface state of the object based on the reflected light,
    wherein the second region comprises at least two sub-regions having different light transmission characteristics from each other.

2. The apparatus of claim 1, wherein the moving stage is configured to move the object at a constant speed.

3. The apparatus of claim 1, wherein the at least two sub-regions comprise a plurality of sub-regions having different shades of a gray scale or a half-tone.

4. The apparatus of claim 1, wherein the light source comprises a white light source, and the at least two sub-regions comprise a red sub-region, a green sub-region, and a blue sub-region.

5. The apparatus of claim 1, wherein the at least two sub-regions comprise a plurality of sub-regions configured to form a polarizer having different polarizing directions.

6. A method of testing an object, the method using a moving stage, a transmissive illuminating optical system, and a detector, wherein the moving stage is configured to hold and move the object, the transmissive illuminating optical system includes a light source generating light and a transmissive mask pattern, the transmissive mask pattern having a first region configured to convert the light generated from the light source into a slit light, and a second region arranged in a movement direction of the object with respect to the first region to partially transmit the light generated from the light source, wherein the transmissive illuminating optical system is configured to project a measuring light, which is provided by transmitting the light generated from the light source through the transmissive mask pattern, to the object, the method comprising:

acquiring a reflected light of the measuring light from the object using the detector; and detecting a height and surface state of the object based on the reflected light acquired by the detector, wherein the second region comprises at least two sub-regions having different light transmission characteristics from each other, wherein the at least two sub-regions are arranged in the movement direction.

7. The method of claim 6, wherein the moving stage is configured to move the object at a constant speed.

8. The method of claim 6, wherein the at least two sub-regions comprise a plurality of sub-regions having different shades of a gray scale or a half-tone.

9. The method of claim 6, wherein the light source comprises a white light source, and the at least two sub-regions comprise a red sub-region, a green sub-region, and a blue sub-region.

10. The method of claim 6, wherein the at least two sub-regions comprise a plurality of sub-regions configured to form a polarizer having different polarizing directions.

11. An apparatus for testing an object, the apparatus comprising:

a moving stage configured to hold and move the object;

a transmissive illuminating optical system including a light source generating light and a transmissive mask pattern, the transmissive mask pattern including a first region configured to convert the light generated from the light source into a slit light, and a second region arranged in a movement direction of the object with respect to the first region to partially transmit the light generated from the light source, wherein the transmissive illuminating optical system is configured to project a measuring light, which is provided by transmitting the light generated from the light source through the transmissive mask pattern, to the object; and a detector configured to receive a reflected light of the measuring light from the object and to detect a height and surface state of the object based on the reflected light, wherein the second region of the transmissive mask pattern comprises at least two sub-regions of different colors or of different polarization directions.

12. The apparatus of claim 11, wherein the light source comprises a white light source, and the at least two sub-regions comprise a red sub-region, a green sub-region, and a blue sub-region.

13. The apparatus of claim 11, wherein the at least two sub-regions comprise a plurality of sub-regions configured to form a polarizer having different polarizing directions.

14. The apparatus of claim 11, wherein the moving stage is configured to move the object at a constant speed.

* * * * *